United States Patent [19]

Evans

[11] 4,069,037
[45] Jan. 17, 1978

[54] SELECTIVE HERBICIDE FOR PINEAPPLE CROPS
[75] Inventor: Arlyn Wayne Evans, Memphis, Tenn.
[73] Assignee: E. I. Du Pont de Nemours and Company, Wilmington, Del.
[21] Appl. No.: 736,453
[22] Filed: Oct. 28, 1976
[51] Int. Cl.$^2$ ............................................. A01N 9/22
[52] U.S. Cl. .................................... 71/93; 544/211
[58] Field of Search ................................................ 71/93
[56] References Cited
U.S. PATENT DOCUMENTS

| 3,873,540 | 3/1975 | Fuchs et al. | 71/93 |
|---|---|---|---|
| 3,902,887 | 9/1975 | Lin | 71/93 |

OTHER PUBLICATIONS

Manvel. Chem. Abst. vol. 60 (1964) 2264f.
Dhuria et al. Chem. Abst. vol. 75 (1971) 75172g.

Primary Examiner—Lewis Gotts
Assistant Examiner—Catherine L. Mills

[57] ABSTRACT

1-Methyl-3-cyclohexyl-6-dimethylamino-s-triazine-2,4(1H,3H)-dione

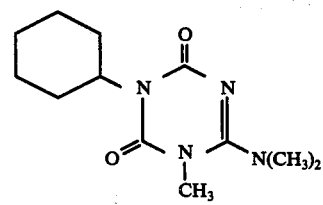

is useful for the selective control of many broadleaved and grassy weeds in pineapple crops.

5 Claims, No Drawings

SELECTIVE HERBICIDE FOR PINEAPPLE CROPS

BACKGROUND OF THE INVENTION

1-Methyl-3-cyclohexyl-6-dimethylamino-s-triazine-2,4(1H,3H)-dione and its use as a broad spectrum herbicide are disclosed in copending U.S. Pat. No. 3,902,887, issued Sept. 2, 1975 to Kang Lin.

Copending U.S. patent application Ser. No. 712,194 filed Aug. 9, 1976 by the inventor hereof, Arlyn Wayne Evans, which is a continuation-in-part of U.S. patent application Ser. No. 700,079, filed July 6, 1976, now abandoned which is in turn a continuation of U.S. patent application Ser. No. 607,896, filed Aug. 26, 1975, now abandoned, discloses and claims the use of 1-methyl-3-cyclohexyl-6-dimethylamino-s-triazine-2,4(1H,3H)-dione as a selective herbicide in sugarcane crops.

The present invention results from the discovery that this compound exhibits selective herbicide activity in pineapple crops as well. That is, it has now been confirmed that this compound, when applied under the proper conditions, will effectively control many broadleaved and grassy weeds in pineapple crops with safety to the crop.

SUMMARY OF THE INVENTION

This invention relates to the use of 1-methyl-3-cyclohexyl-6-dimethylamino-s-triazine-2,4 (1H,3H)-dione

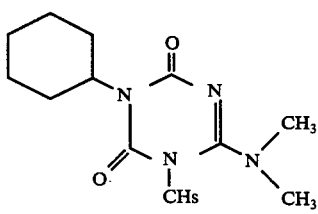

I as a selective herbicide in pineapple crops. The compound of formula I can be applied either preemergence or postemergence with respect to the weeds for the effective control of a variety of broadleaved and grassy species in the above-mentioned crop with safety to the crop, e.g. application can be made prior to planting the crop or as a directed postemergence application after top growth is well advanced.

DESCRIPTION OF THE INVENTION

Synthesis of the compounds

The compound of formula I can be made by the process described and exemplified in U.S. patent application Ser. No. 476,553 now U.S. Pat. No. 3,983,116 and 476,552, identified above, and by the process described and examplified in U.S. Pat. No. 3,850,924, granted Nov. 26, 1974 to Julius Fuchs and Joel B. Wommack.

In addition, the following preferred process, which is the subject of copending U.S. patent application Ser. No. 574,351, filed June 5, 1975 by Adams et al., now abandoned can be used to prepare the compound of formula I:

Equation I represents preparation of the starting material as described in U.S. Pat. No. 3,657,443.

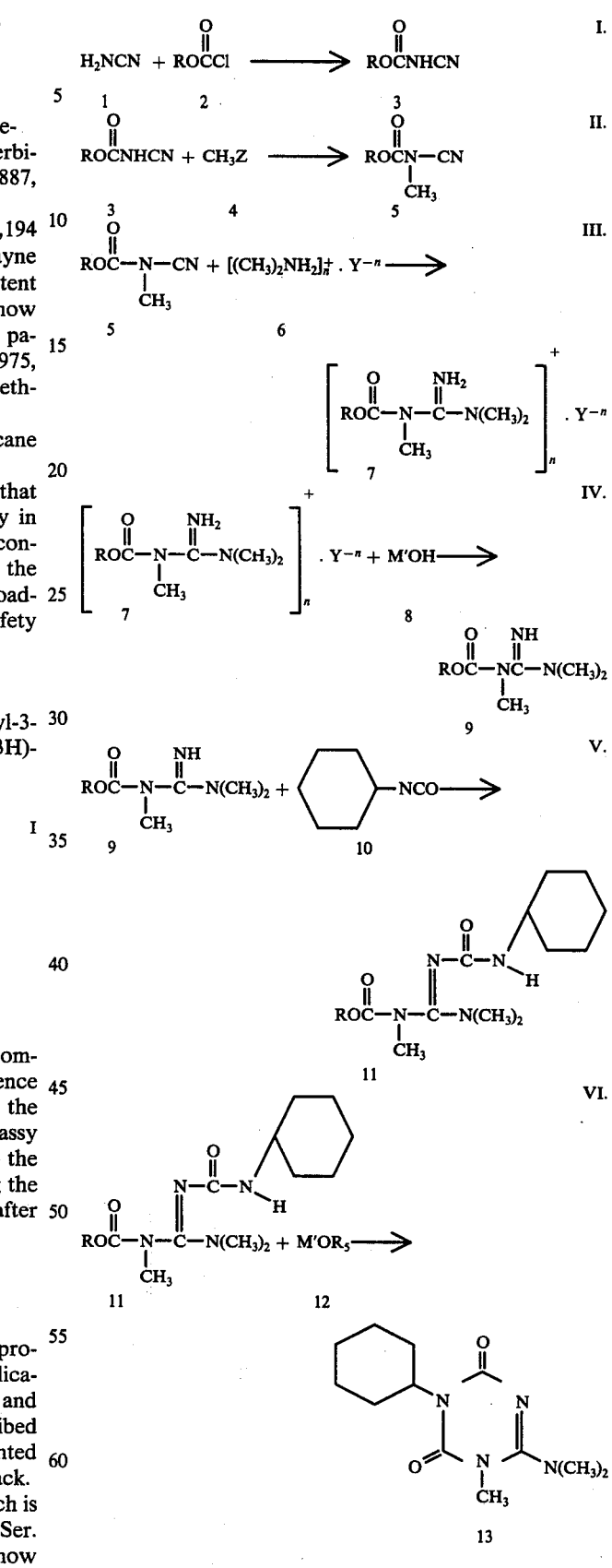

wherein
R is ethyl, n-propyl, or isopropyl;
Y is Cl— or $SO_4=$: $n = 1$ when Y is Cl— and $n = 2$ when Y is $SO_4=$;

Z is iodide, bromide or

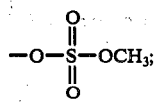

M' is alkali metal; and
$R_5$ is hydrogen or alkyl or 1-4 carbon atoms.

Step I and II are performed sequentially in water. Compound 5 is isolated by separating it from the aqueous brine formed in these reactions.

After the reaction of step III is completed, compound 7 and any unreacted compound 6 must be converted to the free base forms with an alkali metal hydroxide. The untreated amine, $(CH_3)_2NH$, must be removed so that it will not be present in step V.

In the following detailed description, all temperatures are in degrees centigrade and all percentages are by weight unless otherwise stated.

An aqueous solution of the sodium salt of compound 3 containing from 15-35% of compound 3, preferably 20-30%, is reacted at 10°-70°, preferably 40°-45°, with 0.9-2.0, preferably 1.45-1.55 molecular equivalents of an alkylating agent 4 (for example, dimethyl sulfate) during a period of 1-16 hours, preferably 2-4 hours (equation II). Methyl iodide or bromide can be used instead of dimethyl sulfate; the sulfate is preferred for economic reasons.

As the reaction proceeds, a second phase of compound 5 forms. After the reaction has proceeded for the desired time, the upper layer is separated and the lower, aqueous, layer can be discarded, or if economic conditions justify, this layer can be extracted with an organic solvent, preferably toluene, or distilled to recover the small amount of compound 5 contained therein.

The upper layer is added to an aqueous solution containing 15-75% of the amine hydrochloride or 15-45% of the amine sulfate, compound 6, preferably 25-50% of the hydrochloride (equation III). The mole ratio of amine salt to compound 5 can be from 0.8-3, preferably 1.0-1.35. The mixture is then agitated for 0.5-6 hours at 50°-100°, preferably 85°-95° (equation III). Higher temperatures require shorter reaction time and vice versa. It is important to control the pH between 5.8 and 8.0 during reaction III. If the pH is too low, the reaction will be very slow; if the pH is too high, the product 7 will decompose. This control is most conveniently maintained by using electrodes to monitor the pH and adding base, for example, sodium hydroxide, potassium hydroxide, or calcium hydroxide as needed. Sodium hydroxide is preferred.

It should be realized that in these highly concentrated solutions, pH readings may be only coincidentally related to the hydrogen ion concentration. However, when the meters and electrodes are calibrated against a standard buffer before use, the pH response of the electrodes in the reaction mass indicates the state of the reaction.

The resulting reaction mass contains compound 7 and by-product tri-substituted guanidine as well as unreacted compound 6, all present as salts. Before proceeding with step V it is necessary to convert compound 7 into its free base, compound 9. This also converts unreacted compound 6 into free amine, $(CH_3)_2NH$ which is removed to prevent the formation of by-product ureas. This operation can be effected by adding 10-50% aqueous sodium hydroxide until the pH is 11.0 to 12.5 as determined by a glass electrode meter combination and extracting with an organic solvent. Distillation of a portion of the organic solvent used for extraction removes the more volatile amine, $(CH_3)_2NH$. The amine can also be removed directly from the aqueous alkaline solution by distillation. The former procedure is preferred.

The extraction procedure can be performed by passing the aqueous alkaline solution through a continuous counter-current extractor where the organic phase is a solvent such as methylene chloride, benzene, chlorobenzene, toluene, or xylene; toluene is preferred. A batchwise extraction can also be performed. Temperature can vary between 9° and 65° C. The amount of solvent can vary from 0.5 to 10 parts per part aqueous phase, depending on economic factors. The exit organic solvent is sent to a still where amine, $(CH_3)_2NH$, and any entrained water are distilled overhead, leaving a residual solution of compound 9. The concentration of compound 9 will, of course, depend on the operating parameters of the extractor and still.

The residual solution of compound 9 is analyzed by gas chromatography for tri-substituted guanidine and for compound 9. If any guanidine is present, a stoichiometric amount of 5-10% aqueous sulfuric or hydrochloric acid, preferably sulfuric, is added to form the salt of the quanidine.

Isocyanate 10 is now added. The amount added can vary from 0.8 to 1.0 moles of compound 10 per mole of compound 9; 0.90-0.98 is preferred. The resulting reaction mass is stirred at 10°-90° C., preferably 50°-75° C., until the reaction is complete. Reaction time can be from 0.5 to 8 hours.

If less than a stoichiometric amount of compound 10 has been added, the pH is adjusted to 5.5 by adding 5-10% sulfuric or hydrochloric acid; sulfuric is preferred. If acid has been added, the mixture is allowed to settle, and the layers are separated. The lower, aqueous, layer is recycled to the extraction step, and the upper layer is dried by distilling until a constant head temperature is attained either under vacuum or at atmospheric pressure; absolute pressure of 100 to 400 mm Hg is preferred.

If acid is not used, the reaction mass does not have to be distilled. The product 11 can be isolated by concentration and/or cooling of the solution until crystallization occurs followed by filtration or centrifugation. However, it is usually more convenient to carry it forward as a solution to the next step (equation VI).

Compound 9 is subject to decomposition in aqueous solution, particularly under conditions of temperature and pH. Under such conditions it tends to decompose into the corresponding tri-substituted guanidine as illustrated in the following equation:

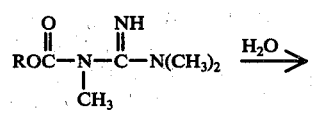

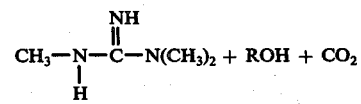

The rate of decomposition is directly proportional to the pH and temperature. Therefore, when removing amine, $(CH_3)_2NH$, by direct distillation from water it is preferred to use a vacuum or inert gas to perform the operation as rapidly as possible.

The above-mentioned aqueous distillation procedure can be operated batch-wise or continuously. It is preferred to carry out the operation in a continuous manner so that the exposure of compound 9 to high temperature and high pH is reduced to a minimum. This is accomplished by adding aqueous alkali metal hydroxide to the product from step III in a pipeline reactor or by running the product and an alkali metal hydroxide into a small agitation vessel with a short hold-up time, no more than 10, preferably no more than 2 minutes. The separate flow rates are adjusted so that the resulting pH is between 11.0 and 13.0. If the concentration of amine salt used is such that alakli metal salt precipitates during this neutralization, additional water should be added to maintain this salt in solution. The overflow from this vessel is fed through a distillation column operated under vacuum. The column is heated by feeding steam into the bottom. Amine, $(CH_3)_2NH$, and water are taken off as distillate overhead and an aqueous solution of compound 9 and tri-substituted guanidine as bottoms.

The conditions under which the column can be operated are selected so that the temperature of the feed through the column is not over 50° C. This necessitates cooling the product from equation III to approximately 30° C before adding the caustic. The column is operated at an absolute pressure of 25–300 mm of mercury, preferably 50–150 mm, and the amount of steam fed to the bottom of the column is adjusted such that the amount of water taken overhead along with the amine is equivalent to 5–25% of the weight of the reaction mass from equation IV.

The bottoms from the above distillation are fed into a hold tank which is maintained at a pH of 5–7 by the continuous addition of either sulfuric or hydrochloric acid; hydrochloric is preferred. The concentration of compound 9 in the neutralized solution is maintained at 15–50% preferably 20–40%. The concentration will depend upon the concentration of the aqueous solution of the amine, the concentration of the base and acid solutions employed in the previous steps, and the amount of concentration or dilution which occurred during the distillation. The temperature of this solution is maintained at 25°–45°, preferably 25°–35°, by either cooling the bottoms in a continuous-type cooler before neutralization or by cooling the neutralization vessel itself.

When the amine has been removed by direct distillation from water, step V is performed by preparing a mixture of the above solution and a solvent such as benzene, chlorobenzene, toluene, or xylene; toluene is preferred. The amount of solvent added should be sufficient to dissolve the amount of compound 11 which will be formed. Generally, the amount of solvent used is about 7–10 times the amount of compound 11 present in the aqueous solution.

An amount of compound 10 which is stoichiometrically equivalent to 85–100%, preferably 90–98%, of compound 9 present in the aqueous layer is now added in one portion or continuously for up to three hours, preferably 30 minutes to one hour and 50% aqueous caustic is added simultaneously with good agitation at a rate which will maintain the pH at 9–10, preferably 9.3–9.7. The caustic addition is continued until the pH is almost constant. The temperature is maintained at 10°–90° C., preferably 35°–50° C., during the addition by external heating and cooling as required. The caustic addition time is from 1–8 hours. The pH is then adjusted to 6.0 with acid. The agitation is stopped and the layers allowed to separate. The lower aqueous layer is removed and the upper organic layer is dried by distilling until a constant head temperature is attained either under vacuum or at atmospheric pressure; absolute pressure of 100–400 mm Hg is preferred.

The solution or slurry containing compound 11 is cooled if necessary to 25°–55° C while anhydrous free dimethylamine is added. It is preferred to add the amine at 25°–55° C, but higher or lower temperatures can be used depending on the solubility of the amine in the particular solvent. It is important to have at least 0.5, and preferably 1.0–8.0, moles of amine per mole of compound 11.

Next the ring closure catalyst (compound 12) is added (equation VI). The catalyst is an alkali metal alkoxide or hydroxide. Alkali metal alkoxides can be added either as dry solid or as a solution in the alkanol. Alkali metal hydroxides can be added as a solution in an alkanol. Dry sodium methoxide or a solution of sodium methoxide in methanol is a preferred catalyst. The amount of catalyst needed is from 0.1 to 5.0 mole percent of compound 11. Higher concentrations are not desirable because side reactions begin to intervene. A preferred concentration of compound 12 is from 2.0 to 4.0 mole percent of compound 11. The temperature is not critical and the ring closure reaction can proceed at temperatures from 0° to 120° provided that the amine is kept within the reaction system. The reaction is normally exothermic and the solution may be cooled if a lower temperature is required to retain the amine. It is critical that the amine remain present until ring closure is about complete.

After the catalyst is added, the reaction mass is held for 15 seconds to 2 hours to insure completion of the ring closure. The reaction is rapid and normally is about complete in less than 15 minutes. The more completely anhydrous the reaction mass, the more rapid is the reaction. An amount of acid equivalent in moles to the amount of the catalyst is added to the reaction mass after ring-closure is complete. This acid neutralizes the catalyst and/or reaction by-products which catalyze product decomposition during the isolation step. Preferably, the acid is added as soon as possible after ring-closure is complete. The type of acid, either organic or inorganic, is not critical; but organic acids are preferred, particularly acetic acid. The added amine, by-product alkanols, and part of the solvent are then removed by distillation either at atmospheric or reduced pressure.

Alternatively, the ring-closure reaction can be performed in a continuous manner. In this embodiment the catalyst is mixed with the reaction mass containing compound 11 and the amine in a pipeline reactor. The acid is added downstream after the temperature rise is complete. The amine, by-product alcohols and part of the solvent are then removed by distillation.

The residue is washed at 30°–100° C., preferably 50°–70° C., with 5% aqueous alkali metal hydroxide, preferably sodium hydroxide, in an amount equal to or slightly greater than (up to 20% molar excess) the amount of catalyst. The layers are allowed to settle, the aqueous layer is removed, and the organic layer is washed with water in an amount approximately equivalent in volume to the caustic wash. Again the layers are allowed to settle, the aqueous layer is removed, and the pH of the wet organic layer is adjusted to 6–7 with acid. (The pH is measured using a glass-calomel combination electrode.) Organic acids are preferred for this operation; acetic acid is especially preferred. This washing procedure removes by-products formed during the ring-closure reaction. If a less pure product is satisfactory, the washing steps can be eliminated.

The product can be isolated from the organic solvent either after the washing operation or without washing, through concentration of the organic phase by distillation. The concentrate is then diluted with a poor solvent for compound 13, e.g., hexane, which caused compound 13 to precipitate. The stable crystalline product is recovered by conventional methods.

In the following examples, all parts are by weight and all temperatures in degrees centigrade unless otherwise indicated.

EXAMPLE 1

A. Synthesis N-ethoxycarbonyl-N-methylcyanamide (Equations I and II)

657 Parts of ethyl chloroformate and 945 parts of a 50% aqueous sodium hydroxide solution were added simultaneously to a solution of 504 parts of a 50% aqueous cyanamide solution in 825 parts of water at 25° during a period of 90 minutes and at a pH of 6.9 to 7.1. As the addition of the reactants progressed, the temperature of the reaction mass was allowed to rise to 53°–55° and was maintained within that range by cooling. When the addition was complete, the reaction mass was cooled to 40°. Dimethylsulfate (1,134 parts) was then added during one hour with stirring while maintaining the pH at 7 to 7.1 by the addition of 50% aqueous sodium hydroxide solution. After holding 3 hours at 40° the resulting two-phase solution was transferred to a separatory funnel. The upper phase of N-ethoxycarbonyl-N-methylcyanamide was separated and the lower aqueous phase was sent to secondary recovery, either distillation or extraction. The upper phase of 669 parts was 93% N-ethoxycarbonyl-N-methylcyanamide (81% yield). This upper phase is usually pure enough for subsequent steps. However, vacuum distillation was used to provide pure N-ethoxycarbonyl-N-methylcyanamide, b.p. 67° at 2.2 mm.Hg.

B. Synthesis of N-ethoxycarbonyl-N,N',N'-trimethylguanidine (Equations III and IV)

A solution of 339 parts of dimethylamine hydrochloride in 500 parts of water was heated to 50° and 458 parts of the upper phase from (A) was added to it. The resulting two-phase mixture was then heated for approximately 2.25 hours at 90° and pH of 6.5, after which time the starting N-ethoxycarbonyl-N-methylcyanamide had nearly completely disappeared. The pH was kept at 6.5 by adding 50% sodium hydroxide as required. The solution was then cooled to 40° and 25% aqueous sodium hydroxide solution was added to reach pH 11.5. Repeated extraction of the reaction solution with toluene and partial evaporation of the toluene gave a solution containing 489 parts of crude N-ethoxycarbonyl-N,N',N'-trimethylguanidine from which the pure product was isolated by distillation at 70°/0.3 mm.Hg.

C. Synthesis of Ethyl N-(N'-cyclohexylcarbamoyl-N,N-dimethylamidino)-N-methylcarbamate (Equation V)

11 parts of cyclohexyl isocyanate was added to 16 parts of N-ethoxycarbonyl-N,N',N'-trimethylguanidine in 150 parts of toluene. The temperature was kept at 50° to 75° for 1.25 hours to complete reaction. The product, ethyl-N-(N-cyclohexylcarbamoyl-N',N'-dimethylamidino)-N-methyl-carbamate was isolated by crystallization, filtration, and drying, m.p. 97°–98°. Preferably, however, it is kept as a toluene solution carried forward as such to the next step (Equation V).

D. Synthesis of 1-methyl-3-cyclohexyl-6-dimethylamino-s-triazine-2,4(1H,3H)dione (Equations II, III, IV, V)

A 50% stoichiometric excess of dimethylsulfate (1234 parts) was added at 40° during one hour with agitation to 3141 parts of an aqueous solution containing 888 parts of the sodium salt of compound 3 (R = ethyl) which had been adjusted to pH 7 with 50% aqueous sodium hydroxide. The reaction was allowed to continue for three hours while the temperature was maintained at 40° by external heating or cooling and at pH 7 by the addition of 50% aqueous sodium hydroxide as required. During the reaction a separate phase of compound 5 (R = ethyl) was formed.

When the reaction was about complete, the agitation was stopped and the layers allowed to separate. The upper layer of 728 parts was 93% pure compound 5 (R = ethyl). It was separated and added to 1,200 parts of an aqueous solution containing 540 parts of dimethylammonium chloride. The resulting mixture was heated to 90° and stirred for 2.25 hours at pH 6.5. The pH was maintained at 6.5 by adding 50% sodium hydroxide as required. The solution was then fed into a mixing tee along with 25% aqueous sodium hydroxide. The separate feed rates were adjusted so that the effluent from the tee was kept at pH 11.0–11.5. The effluent from this vessel was fed into the top of a continuous counter-current extractor, which operates as a 5 theoretical plate column. Toluene was fed into the bottom of the column at a rate of 2.25 pounds of toluene per pound of aqueous feed. The toluene solution at the top of the column overflows into an amine stripper.

In the stripper, excess dimethylamine, entrained water, and some toluene solvent are distilled overhead through a packed column. The residual toluene solution of 7743 parts contained 777 parts of compound 9 (R = ethyl). Analysis showed by-product 1,1,3-trimethylguanidine to be present in this residue, and a small amount of sulfuric acid solution was added to exactly neutralized all the 1,1,3-trimethylguanidine but little or none of compound 9.

507 Parts of cyclohexylisocyanate was added to this residue. The mixture was then stirred at 50°–75° for 1.25 hours. It was cooled to 40° and sulfuric acid solution was added with good stirring until the pH of the aqueous phase was 5.5. The organic phase was separated and dried by brief azeotropic distillation at a pressure of 100 mm mercury. The organic phase of 8,200 parts contained 1,205 parts of compound 11 (R = ethyl).

Dimethylamine (1,095 parts) was added to the solution of compound 11 while the temperature was maintained at 25°–50° by external cooling. Then 35 parts of a 25% solution of sodium methoxide in methanol was added with good agitation. The reaction is slightly exothermic and the temperature increased 4° during 15–45 seconds. The reaction was allowed to continue for an additional two minutes; then 9.72 parts of acetic acid were added. The solution was then distilled until a constant 110° head temperature showed that dimethylamine and by-product alkanols have been completely removed. The still bottoms were cooled to 60° and washed with a small quantity of 5% sodium hydroxide followed by a small quantity of water. The amount of sodium hydroxide was calculated so that it was equivalent in moles to the acetic acid added earlier.

The toluene phase was then concentrated by distillation until the concentration of compound 13 reached 50% by weight. The residue was cooled to 40° and stirred while n-hexane was added slowly.

The weight of n-hexane used was 80% of the total weight of the 50% solution. During the n-hexane addition the solution was seeded with compound 13. The crystals were recovered by filtration and dried to give 920 parts of compound 13 m.p. 112°–115° C.

Formulation and use of the compound

The compound of formula I is useful for control of undesired vegetation in pineapple crops; i.e. the compound of formula I can be used to control a variety of broadleaved and grassy weeds and even weed trees in the above-mentioned crop with safety to said crop.

The precise amount of compound to be used in any given situation will vary according to the time of treatment, the weed species and soil type involved, the formulation used, the mode of application, prevailing weather conditions, particularly rainfall, foliage density and like factors. In addition, the crop variety and age of planting should be taken into consideration.

In any event, use rates necessary to provide effective control, even with respect to many weed species that are resistant to other herbicides, are quite low. Since so many variables play a role, it is not possible to state the rate of application suitable for all situations. However, broadly speaking, the compound of formula I is used at levels of about 0.25 kg/ha to about 4 kg/ha. The lower rate given here will provide only a brief effect on weeds under many use conditions. The higher rate, on the hand, will be excessive and can cause crop injury except where soils have a high colloidal content, where the more resistant crop varieties are grown, or where the crop plants are well established. The most preferred rate is in the range of about 0.5 to about 1 kg/ha.

The application may be made prior to planting or as a directed postemergence spray after top growth is well advanced. Applications may be broadcast (i.e., cover the entire surface of the field) or limited to only a portion such as a band over the row. Preemergence applications are most effective when made within a few weeks prior to expected germination of the weed species. Postemergence applications are preferably made during the period of active growth of the weed species. The applications may be made prior to the planting of the desirable crop species or to land on which they are already present. In the latter case, treatment is best applied either before or well after the period of most active growth of the crop. Successful applications may be made during the active growing season, however, if case is taken to avoid foliage. In all instances, the treatment should be applied uniformally.

Proper application of this compound results in good control of many serious and troublesome weeds that may occur in pineapple fields. Some of the many different weed species controlled are wild turnip (*Brassica campestris*), johnsongrass seedlings (*Sorghum halepense*), common ragweed (*Ambrosia artemisifolia*), showy crotalaria (*Crotalaria spectabilis*), violet crabgrass (*Digitaria violascens*), common crabgrass (*Digitaria sanguinalis*), foxtail (*Setaria sp.*) pigweed (*Amaranthus sp.*), Florida beggarweed (*Desmodium tortuosum*), cocklebur (*Xanthium pennsylvanicum*), morningglory (*Ipomoea sp.*), carpetweed (*Mollugo verticillata*), smartweed (*Polygonum sp.*), goosegrass (*Eleusine indica*), curly dock (*Rumex crispus*), burning nettle (*Urtica urens*), common yarrow (*Achillea millefolium*), chicory (*Cichorium intybus*). guineagrass (*Panicum maximum*). torpedograss (*Panciun repens*), purslane (*Portulaca oleracea*). barnyardgrass (*Echinochloa crusgalli*), dalligrass (*Paspalum dilatatum*), vaseygrass (*Paspalum urvillei*), catsear (*Hypochaeris sp.*), chickweed (*Stellaria media*), goldenrod (*Solidago sp.*), darnel (*Lolium temulentum*), smooth crabgrass (*Digitaria ichaemum*), coffee senna (*Cassia occidentalis*), lambsquarters (*Chenopodium album*), henbit (*Lamium amplexicaule*), crowfoot (*Ranunculus sp.*), wild euphorbia (*Euphorbia sp.*), *Ageratum conyzoides, Digitaria ciliaris, Synedrella vialis, Richardia brasiliensia, Dactyloctenium aegyptium, Eragrostis tenella*, fescue (*Festuca spp.*), panic grass (*Panicum spp.*), orchard grass (*Dactylis glomerate*), vaseygrass (*Paspalum urvillei*), quackgrass (*Agropyron repens*), broomsedge (*Andropogon virginicus*), sweet vernal grass (*Anthoxanthum odoratum*), bluegrass (*Poa spp.*), bermudagrass (*Cynodon dactylon*), brackfern (*Pteris aquilina*), wild carrot (*Daucus carota*), horseweed (*Erigeron canadensis*), campion (*Silene stellata*), Canada thistle (*Cirsium arvense*), ragwort (*Senecio spp.*), broom (*Cytisus spp.*), honeysuckle (*Lonicera japonica*), brambles (*Rubus spp.*), wild grape (*Vitis spp.*), groundsel tree (*Baccharis halimifolia*), toetoe (*cortaderia spp.*), persimmon (*Diospyros virginiana*), red maple (*Acer rubrum*), red gum (*Liquidambar styraciflua*), eucalyptus (*Eucalyptus regnans*), post oak (*Quercus stellata*), blackjack oak (*Quercus marilandica*), hackberry (*Celtis occidentalis*), and sassafras (*Sassafras variifolium*), and nutsedge (*Cyperus sp.*). Of particular interest is the high activity of the compound of this invention on actively growing nutsedge.

The compound of formula I can be used for weed control in pineapple crops, either along or in combination with other herbicices. An important function of the added herbicide is to prolong the period of weed control obtained. Compounds particularly effective for this purpose are diuron [3-(3,4-dichlorophenyl)-1,1-dimethyl-urea], linuron [3-(3,4-dichlorophenyl)-1-methoxy-1-methyl-urea], bromacil [3-(sec-butyl)-5-bromo-6-methyluracil], terbacil [3-tert-butyl-5-chloro-6-methyluracil], and metribuzin [4-amino-6-tert-butyl-3-methylthio-1,2,4-triazine-5-one]. For example, the compound of formula I can be combined with diuron in ratios (by weight) of from 1:1 to 1:8, preferably 1:1 to 1:4. The optimum ratio between the compound of formula I and the additional herbicide can be readily determined by a person of ordinary skill in the art of weed control.

The compound of formula I can be formulated in the various ways which are conventional for herbicides of similar physical properties. Useful formulations include wettable and soluble powders, suspensions, and solutions in solvents and oils, aqueous dispersions, dusts, granules, pellets, and high-strength compositions. Broadly speaking, these formulations consist essentially of about 1–99% by weight of herbicidally active material and at least one of a. about 0.2–20% by weight of surface active agent, and b. about 5–99% by weight of solid or liquid diluent.

More specifically, the various types of formulations will generally contain these ingredients in the following approximate proportions:

|  | PERCENT BY WEIGHT | | |
|---|---|---|---|
|  | Herbicide | Diluent | Surfactant |
| Wettable Powders | 25–90 | 0–74 | 1–10 |
| Suspensions or Solutions | 5–50 | 40–95 | 0–10 |
| Aqueous Dispersions | 10–50 | 40–89 | 1–10 |
| Dusts | 1–25 | 70–99 | 0–5 |
| Granules and Pellets | 1–35 | 65–99 | 0–15 |
| High-Strength Compositions | 90–99 | 0–10 | 0–2 |

The manner of making and using such herbicidal formulations is described in numerous patents. See, for example, Luckenbaugh, U.S. Pat. Nos. 3,309,192; 3,235,357: Todd, 2,655,445; Hamm et al., 2,863,752; Scherer et al., 3,079,244, Gysin et al., 2,891,855; and Barrous, 2,642,354.

EXAMPLE II

| Solution | |
|---|---|
| 1-methyl-3-cyclohexyl-6-dimethyl-amino-s-triazine-2,4(1H,3H)-dione | 25.5% |
| ethylene glycol monobutylether | 53.2% |
| ethanol | 8.1% |
| water | 13.2% |

The ingredients were combined, warmed and stirred to produce a solution which was subsequently extended with water for spraying.

EXAMPLE III

| Wettable Powder | |
|---|---|
| 1-methyl-3-cyclohexyl-6-dimethyl-amino-s-triazine-2,4(1H,3H)-dione | 25% |
| diatomaceous earth | 71.5% |
| dioctyl sodium sulfosuccinate | 1.5% |
| low viscosity methyl cellulose | 2% |

The ingredients can then be thoroughly blended and passed through a hammer mill to produce particles mostly all below 100 microns.

EXAMPLE IV

| 1.5% Granule | |
|---|---|
| 1-methyl-3-cyclohexyl-6-dimethyl-amino-s-triazine-2,4(1H,3H)-dione | 1.5% |
| Athapulgus clay granules | 98.5% |

The active ingredient was dissolved in an ethanol-water mixture and sprayed onto a bed of the clay granules rotating in a mixer. The granules were removed and dried in a vacuum over prior to packaging.

EXAMPLE V

| Water soluble Powder | |
|---|---|
| 1-methyl-3-cyclohexyl-6-dimethyl-amine-s-triazine-2,4(1H,3H)-dione | 94% |
| zeolex 7A | 3.8% |
| sugar | 1.0% |
| methocel F-50 | 1.0% |
| aerosol OT-B | .2% |

The ingredients were thoroughly blended and passed through a hammer mill to produce particles mostly below 100 microns.

The selective herbicidal activity of the compound of formula I has been tested under varied climate and soil conditions. The following tests are considered representative in demonstrating selective herbicidal activity of the compound of formula I when used under appropriate conditions.

EXAMPLE VI

3-Cyclohexyl-6-(dimethylamino)-1-methyl-1,3,5-triazine-2,4(1H,3H)-dione (I) was applied preemergence to the weeds on the day after planting Smooth Cayenne pineapple. The test was conducted in Columbia on a loam containing 2.5% organic matter. The data below, taken 8 weeks after application, demonstrate good control of *Digitaria sanguinalis* (DS), *Elusine indica* (EI), *Cynodon dactylon* (CD), and *Euphorbia hirta* (EH) with adequate safety to pineapple.

| TREATMENT | RATE (KG/HA) | % WEED CONTROL | | | | % CROP INJURY |
|---|---|---|---|---|---|---|
|  |  | DS | EI | CD | EH |  |
| I | 1 | 93.1 | 54.5 | 71.4 | 100 | 0 |
|  | 2 | 94.1 | 92.3 | 86.6 | 100 | 0 |
|  | 4 | 99.3 | 96.3 | 89.5 | 100 | 12.5 |
| Untreated | — | 0 | 0 | 0 | 0 | 0 |

The following data was taken 12 weeks after application in a test substantially identical to that described above. These data demonstrate good control of *Portulaca oleracea* (PO) as well as the four species previously mentioned.

| TREAT-MENT | RATE (kg/ha) | % WEED CONTROL | | | | | % CROP INJURY |
|---|---|---|---|---|---|---|---|
|  |  | DS | EI | PO | CD | EH |  |
| I | 1 | 90.6 | 85.5 | 80.6 | 37.8 | 100 | 0 |
|  | 2 | 90.3 | 90.9 | 67.7 | 88.3 | 100 | 2.5 |
|  | 4 | 97.0 | 87.3 | 73.4 | 92.1 | 100 | 22.5 |
| Untreated | — | 0 | 0 | 0 | 0 | 0 | 0 |

EXAMPLE VII

In Columbia, 3-cyclohexyl-6-(dimethylamino)-1-methyl-1,3,5-triazine 2,4 (1H, 3H)-dione (I) was applied as a directed and non-directed (over the top) spray to pineapple slips planted 1½ weeks earlier. Weeds were in the 2–5 leaf stage. The soil was a clay loam containing 1.8% organic matter. The herbicide provided commercially acceptable (rating of 7.0 or more) weed control with adequate safety to the crop (20% or less).

| TREATMENT | RATE (KG/HA) | % WEED CONTROL BROADLEAVES | GRASSES | % CROP INJURY |
| --- | --- | --- | --- | --- |
| I Directed | 1 | 67 | 57 | 0 |
| | 2 | 90 | 70 | 0 |
| | 4 | 100 | 93 | 20 |
| I Over top | 1 | 83 | 77 | 0 |
| | 2 | 100 | 87 | 20 |
| | 4 | 100 | 90 | 50 |
| Untreated | — | 0 | 0 | 0 |

EXAMPLE VIII

A non-directed spray of 3-cyclohexyl-6-(dimethylamino)-1-methyl-1,3,5-triazine-2,4-(1H, 3H)-dione (I) was applied preemergence to weeds in first ratoon pineapple in South Africa. *Paspalum dilatatum, Panicum sp* and *Euphorbia prostrata* were controlled at rates providing adequate safety to the crop.

| TREATMENT | RATE (KG/HA) | WEED CONTROL | CROP INJURY |
| --- | --- | --- | --- |
| I | 1.0 | Satisfactory commercial control | 0 |
| | 2.0 | " | 0 |
| | 4.0 | " | Slight |
| | 6.0 | " | Severe |

EXAMPLE IX

In Hawaii, 3-cyclohexyl-6-(dimethylamino)-1-methyl-1,3,5-triazine-2,4 (1H, 3H)-dione (I) was applied postemergence to ratoon pineapple infested with *Paspalum urvillei* from 1 decimeter tall to just above the pineapple. The soil was a silt loam. The weed control and crop tolerance data below were taken 5½ months after treating. There was satisfactory weed control and crop tolerance.

| TREATMENT | RATE (KG/HA) | % CONTROL OF PASPALUM URVILLEI | % CROP INJURY |
| --- | --- | --- | --- |
| I* | ½ | 48 | 0 |
| | 1 | 72 | 0 |
| | 2 | 80 | 0 |
| | 4 | 92 | 13 |
| | 16 | 100 | 67 |
| Hand Weeded Check | | 100 | 0 |

*Included 1 pt. "Best-wet" spreader activator/100 gallons finished spray.

EXAMPLE X

First ratoon pineapple in Hawaii was treated soon after harvest with 3-cyclohexyl-6-(dimethylamino)-1-methyl-1,3,5-triazine-2,4 (1H, 3H)-dione (I). The pineapple was growing in a clay loam soil and was infested with young seedlings of *Paspalum urvillei*. The data below were recorded 5 months after treatment. Weed control was satisfactory with adequate tolerance of the crop.

| TREATMENT | RATE (KG/HA) | % CONTROL PASPALUM URVILLEI | % CROP INJURY |
| --- | --- | --- | --- |
| (I)* | ½ | 100 | 0 |
| | 1 | 100 | 0 |
| | 2 | 100 | 10 |
| | 4 | 100 | 60 |
| | 8 | 100 | 100 |
| Untreated | — | 0 | 0 |

*Included ½% spreader.

EXAMPLE XI

A pineapple field in Hawaii was prepared by fumigating and mulching. 3-cyclohexyl-6-(dimethylamino)-1-methyl-1,3,5-triazine-2,4 (1H, 3H)-dione (I) was applied as a broadcast treatment over the plastic mulch and bed middles. The clay loam field was then planted to Smooth Cayenne pineapple 2 weeks later. There was adequate control of a mixed weed polulation including *Panicum maximum, Crotalaria spectabilis, Ipomoea pentaphylla* and *Digitaria violascens* with commercially acceptable crop tolerance

| TREATMENT | RATE (KG/HA) | % BARE GROUND | % CROP INJURY* |
| --- | --- | --- | --- |
| (I) | ½ | 75 | 10 |
| | 1 | 63 | 27 |
| | 2 | 85 | 25 |
| | 4 | 90 | 35 |
| Untreated | — | 63 | 35 |

*Includes injury due to weed competition as well as any that might have been caused by the chemical.

I claim:

1. Method for preventing and controlling undesired vegetation in pineapple crops without causing significant injury to said crop comprising applying to the locus of said crop an effective amount of 1-methyl-3-cyclohexyl-6-dimethylamino-s-triazine-2,4(1H,3H)-dione.

2. Method of claim 1 wherein the triazine is applied at a rate of 0.25 to 4.0 kilograms per hectare.

3. Method of claim 1 wherein the triazine is applied at a rate of 0.5 to 1.0 kilograms per hectare.

4. Method of claim 1 wherein the triazine is applied preemergence.

5. Method of claim 1 wherein the triazine is applied postemergence after top growth of the pineapple is well started.

* * * * *